(12) United States Patent
O'Hamill et al.

(10) Patent No.: US 12,728,030 B2
(45) Date of Patent: Sep. 8, 2026

(54) HERNIA BELT OSTOMY SUPPORT SYSTEM

(71) Applicant: Stealth Belt, Inc., Johnson City, TN (US)

(72) Inventors: Richard O'Hamill, Johnson City, TN (US); Rita Hamill, Johnson City, TN (US)

(73) Assignee: Stealth Belt, Inc., Johnson City, TN (US)

( * ) Notice: Subject to any disclaimer, the term of this patent is extended or adjusted under 35 U.S.C. 154(b) by 0 days.

(21) Appl. No.: 19/083,085

(22) Filed: Mar. 18, 2025

(65) Prior Publication Data

US 2025/0352387 A1 Nov. 20, 2025

Related U.S. Application Data

(63) Continuation of application No. 18/667,848, filed on May 17, 2024, now abandoned, which is a continuation of application No. 16/775,681, filed on Jan. 29, 2020, now abandoned.

(60) Provisional application No. 62/799,417, filed on Jan. 31, 2019.

(51) Int. Cl.

| | |
|---|---|
| ***A61F 5/449*** | (2006.01) |
| ***A41D 13/12*** | (2006.01) |
| ***A61F 13/14*** | (2006.01) |

(52) U.S. Cl.
CPC .......... *A61F 5/449* (2013.01); *A41D 13/1254* (2013.01); *A61F 13/148* (2013.01)

(58) Field of Classification Search
CPC .......... A61F 5/449; A61F 5/03; A61F 13/148; A41F 9/002; A41F 9/025; A44B 11/12; Y10T 29/49826; A41D 13/1254; A41D 27/201; A45C 13/103
See application file for complete search history.

(56) References Cited

U.S. PATENT DOCUMENTS

| | | | | |
|---|---|---|---|---|
| 6,568,852 | B1 * | 5/2003 | Godshaw | A45C 7/0068 190/103 |
| 2014/0081189 | A1 * | 3/2014 | Ingimundarson | A61F 5/028 602/19 |
| 2015/0282541 | A1 * | 10/2015 | Appeldoorn | A61F 5/449 2/247 |
| 2017/0202700 | A1 * | 7/2017 | Gallant | A61F 5/449 |
| 2017/0348140 | A1 * | 12/2017 | Riedel | A61F 5/449 |

* cited by examiner

*Primary Examiner* — Guy K Townsend
*Assistant Examiner* — Alessandro R Del Priore
(74) *Attorney, Agent, or Firm* — Much Shelist P.C.

(57) ABSTRACT

The present hernia belt ostomy support system is designed to provide support to a hernia and house a medical device (e.g., an ostomy appliance) within a compartment, wherein the device is comfortable, supportive, inconspicuous, and aesthetically pleasing.

12 Claims, 10 Drawing Sheets

HERNIA BELT OSTOMY SUPPORT SYSTEM

CROSS-REFERENCE TO RELATED APPLICATIONS

This application comprises a continuation application of U.S. patent application Ser. No. 18/667,848 filed on May 17, 2024, which claims the benefit of priority to U.S. patent application Ser. No. 16/775,681 filed on Jan. 29, 2020, which claims the benefit of priority to U.S. Provisional Application 62/799,417 filed on Jan. 31, 2019, the entireties of which are incorporated by reference herein.

BACKGROUND OF THE INVENTION

The present subject matter relates generally to a therapeutic support belt for hernia patients and patients at risk for hernias following surgery involving stoma creation.

Parastomal hernias are a common complication following stoma creation and its prevalence is expected to increase. Reports of the incidence of parastomal hernias vary from 6.5% to as high as 62.5%. A parastomal hernia often leads to a decrease in the quality of life for patients due to discomfort, pain, frequent ostomy appliance leakage, or peristomal skin irritation and can result in significantly increased healthcare costs. Clinical manifestations include an unsightly or bothersome bulge adjacent to the stoma, difficulty pouching, difficulty maintaining a seal when a new pouch is applied, pressure or discomfort associated with stretching of the hernia ring, and intermittent bowel obstructions or acute abdominal pain associated with incarceration of the bowel within the hernia sac. Unfortunately, patients who are symptomatic from a parastomal hernia often suffer from poor quality of life.

For example, patients with hernias often feel a pressure of pain resulting from gravity pulling down on the hernia. For example, in cases of odd shaped, very large hernias, and/or elongated, ridge hernias, the weight and pressure often becomes unbearable causing chronic pain issues and/or skin issues. Further, skin problems can result when the hernia is so cumbersome that it lies directly on the skin, causing rubbing and irritation.

For example, patients that are not candidates for surgery or waiting on surgery are required to bare the pain and pressure sometimes indefinitely. As a result, patients are in need of a hernia support to ease the pain and pressure. Further, people with hernias may feel self-conscious about being seen by others because of their protruding hernia. Patients following surgery involving stoma creation are also in need of proper support to reduce the likelihood of the onset of a parastomal hernia.

Conventional hernia supports do not adequately address necessary support for the abdomen, the area immediately surrounding the stoma, and the ostomy appliance, and often offer one type of support, when in reality varying degrees of support are needed for different patients, different types of hernias, and different types of activities. For example, a different type or level of support may be needed for a hernia patient while reclining and reading a book as compared to running. Vigorous activity, such as running, may be particularly painful and uncomfortable for a hernia patient due to the bouncing motion.

For patients that undergo stomal surgery and are at risk for the development of a parastomal hernia, or have developed a hernia, a variety of factors present including physical, emotional, social, and psychological aspects. For example, dealing with the physical limitations that arise from the hernia, dealing with the additional loss of a body part such as a colon, and/or dealing with the functioning of the ostomy and physical care requirements of the hernia. Further, after surgery, many patients may not wish to make the details of their surgery or physical condition known to others. As a result, devices that are less conspicuous are preferred.

A disadvantage of conventional hernia support devices is that the conventional devices fail to allow ample support around a hole for the stoma, especially at the top edge of the belt, which results in the top of the hernia and/or the top of the flange patch being exposed and unsupported. Further, conventional hernia support devices do not provide appropriate support and concealment for the ostomy appliance. Further, conventional hernia devices typically use cotton or other inadequate materials that absorb large quantities of water and moisture resulting in support product being too cumbersome, heavy, and difficult to wear when wet.

Moreover, conventional support devices fail to adequately cover and support the ostomy bag. The weight of the ostomy bag can often further complicate issues with a hernia. Therefore, the lack of ostomy bag support means that the bag pulls on the skin.

Accordingly, there is a need for a hernia supportive device that provides appropriate support for the abdomen, the area immediately surrounding the stoma, and the ostomy appliance and that is less cumbersome, and more comfortable and supportive, while at the same time being inconspicuous.

BRIEF SUMMARY OF THE INVENTION

The present disclosure provides a hernia belt ostomy support system designed to house a medical device (e.g., an ostomy appliance) within a compartment, wherein the device is comfortable, supportive, inconspicuous, and aesthetically pleasing. Various examples of the methods are provided herein.

Specifically, the present hernia belt ostomy support system provides an adjustable support belt to assist in preventing parastomal hernias and to mitigate the adverse impacts of parastomal hernias when they develop, wherein support is provided in the abdominal area, the area immediately surrounding the stoma, and for the ostomy appliance. Further, the system is inconspicuous, yet functional to maintain support during user motion. Specifically, the present device minimizes movement of the hernia through its multiple elements of support working together. The present system provides inward support for the hernia that protrudes from the body, upward support that works to counteract the downward pressure from gravity, and flexible and expandable outside panel support of the ostomy appliance system by holding it in place against the body. The belt can be worn around the body at the level of the stoma. The system can be fastened on with a dual closure system that can be made of hook and loop. The abdomen can be supported by the body panel that presses in towards the body, the stomal area can be supported by an appropriately reinforced and sized opening, and the ostomy appliance can be supported by a built-in compartment system. The interior compartment can be accessed via any suitable mechanism including, but not limited to, flaps, overlapping panel portions, zippers, clasps, hook and loop systems, among others.

The present hernia support belt system is configured to prevent and/or delay the onset of parastomal hernias, as well as mitigate the adverse impacts of parastomal hernias in the event they have occurred. The present system does this through a unique design that combines abdominal support, specific support around the stoma, and a pouching system to support and conceal the appliance, all structured with a design and use of materials that maximizes function and aesthetic appearance.

With respect to prevention, the present system provides an ability to provide meaningful support for the abdomen, the area immediately surrounding the stoma, and the appliance itself. Not only does this support system provide direct pressure and reinforcement designed to reduce the incidence of parastomal hernias, it also provides increased confidence and security to allow appropriate physical activity levels. Such appropriate physical activity, and abdomen strength, is also associated with a reduced incidence of parastomal hernias (i.e., exercise and use of a support belt can reduce the incidence of parastomal hernias). The present system also has additional aesthetic and functional benefits given its ability to provide necessary support and security in a product that is discrete, made of appropriate materials, and that does not have the appearance of a medical device.

The present system includes a uniquely designed structure to provide additional support directly over the stoma area to enhance the overall effectiveness of the hernia support system. The curved design helps to apply gentle pressure to the area surrounding the hernia while providing less pressure on the stoma itself. The present system provides more support where needed and less where it is not needed. The patient is able to adjust the amount of pressure needed for optimum support and comfort.

To mitigate adverse impacts in the event of a parastomal hernia, the present support belt has benefits in terms of providing support for the weight of the hernia, providing necessary pressure on the hernia inward towards the body to minimize the body profile, and providing triple support for the abdomen, the hernia, and the ostomy appliance.

An advantage of the present disclosure is that it provides a hernia belt system that provides a variable closure option that allow a full range of support for different hernia types, patient size, and activity level. Varying degrees of support are optimal when doing different types of activities and to address individual needs. The variable closure option allows for a user to adjust the level of support, tightness, and/or circumference of the belt system. Support requirements differ for example between being seated reading a book as compared to running. These different levels of activity, or individual preferences, require different degrees of tightness for optimal support levels.

An advantage of the present system is providing non-surgical support for the weight of the hernia and/or ostomy appliance, wherein the device provides pressure on the hernia inward towards the body to minimize the body profile.

A further advantage of the present system is providing support to a patient without having the appearance of a user wearing a medical device.

Another advantage of the present system is providing hernia support to pull the hernia closer into the body such that the profile of the user does not show a protrusion.

Another advantage of the present system is allowing a non-surgical patient and/or post-surgical patient the confidence to feel normal and return to normal activities, as the hernia belt ostomy support system provides for concealment of the ostomy appliance and does not have the appearance of a medical device.

Another advantage of the present system is providing a hernia belt ostomy support system that a user can wear to go to the beach or swimming without the hernia and ostomy appliance being visible. Conventional devices provide poor support to the hernia and appliance when wet.

Another advantage of the present system is providing protection of the hernia such that patients do not feel the need to constantly use their hands to hover over the hernia area to protect the hernia or cover the hernia from view. A patient wearing the presently disclosed hernia belt can feel secure and protected.

Additional objects, advantages and novel features of the examples will be set forth in part in the description which follows, and in part will become apparent to those skilled in the art upon examination of the following description and the accompanying drawings or may be learned by production or operation of the examples. The objects and advantages of the concepts may be realized and attained by means of the methodologies, instrumentalities and combinations particularly pointed out in the appended claims.

BRIEF DESCRIPTION OF THE DRAWINGS

The drawing figures depict one or more implementations in accord with the present concepts, by way of example only, not by way of limitations. In the figures, like reference numerals refer to the same or similar elements.

DETAILED DESCRIPTION OF THE INVENTION

Figures 1, 2:
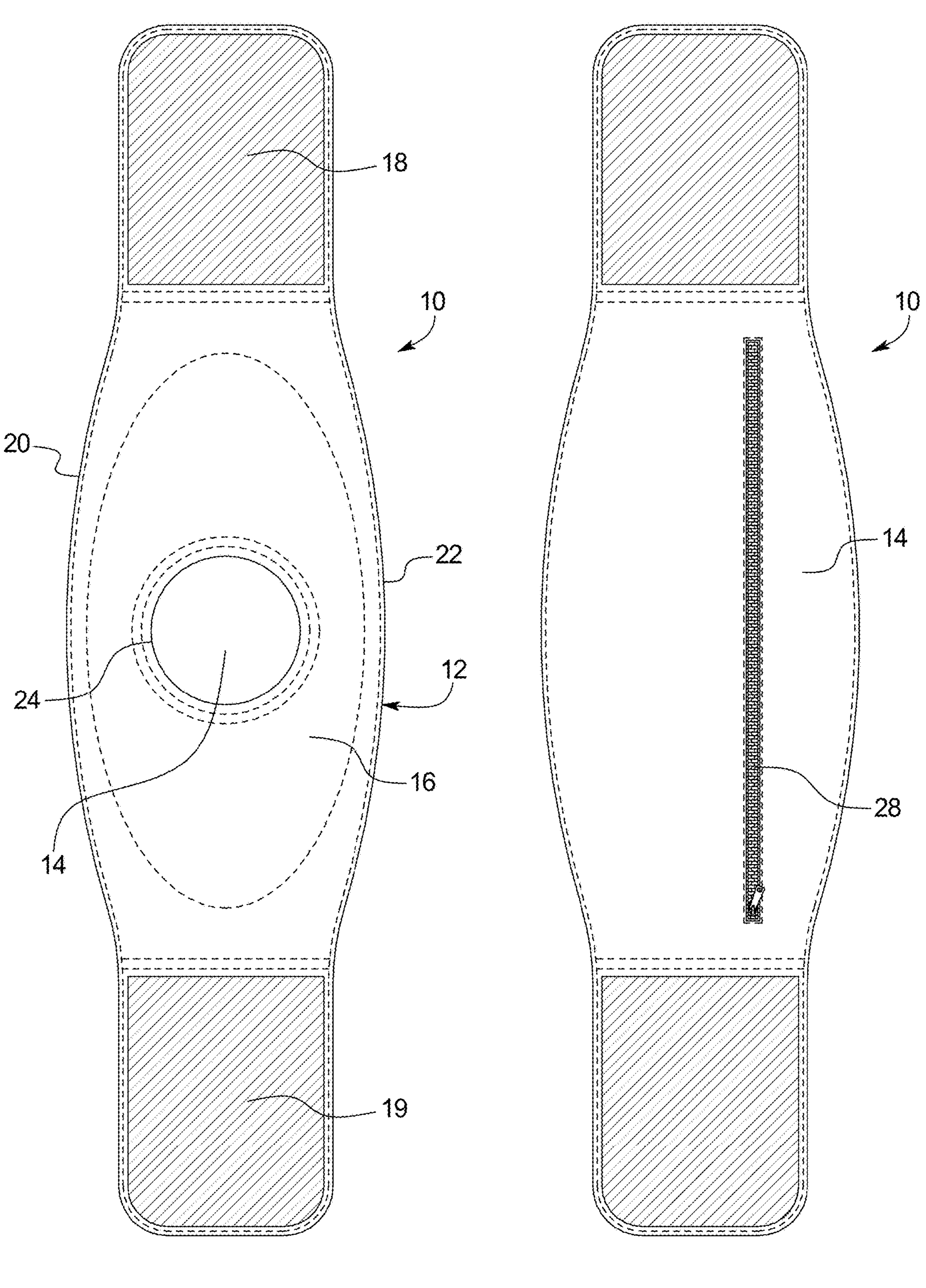
FIG. 1 is a back view of an example of the hernia ostomy support device disclosed herein.
FIG. 2 is a front view of an example of the hernia belt ostomy support system disclosed herein.

As shown in FIG. 1, the present hernia belt ostomy support system 10 can include a front body portion 12 and a back body portion 30. The front body portion 12 can include a front panel 14 and a back panel 16, as well as two side portions 18, 19 that can include a fastening mechanism. The back panel 16 of the front body portion 12 can include a stoma opening 24 to provide access to the stoma for the appliance. The front body portion 12 can include a top edge 20 and bottom edge both 22 extending from a first end 18 to a second end 19. The top edge 20 and/or bottom edge 22 of the front body portion 12 can include curvature away from the center. In an example, the curvature of at least one of the edges provides ample (e.g., 2-5 inches) allowance above the stoma opening 24 to improve support to the potential hernia area or the hernia.

The belt body first end 18 and second end 19 can be removably connected to each other and/or to back body portion 30 of the belt body via any suitable closing mechanism including, but not limited to, hook and loop, clasps, buttons, fasteners, snaps, among others. Further, the fastener can provide a range of adjustability to account for different sized patients, hernias, and activities.

Figures 3A, 3B:
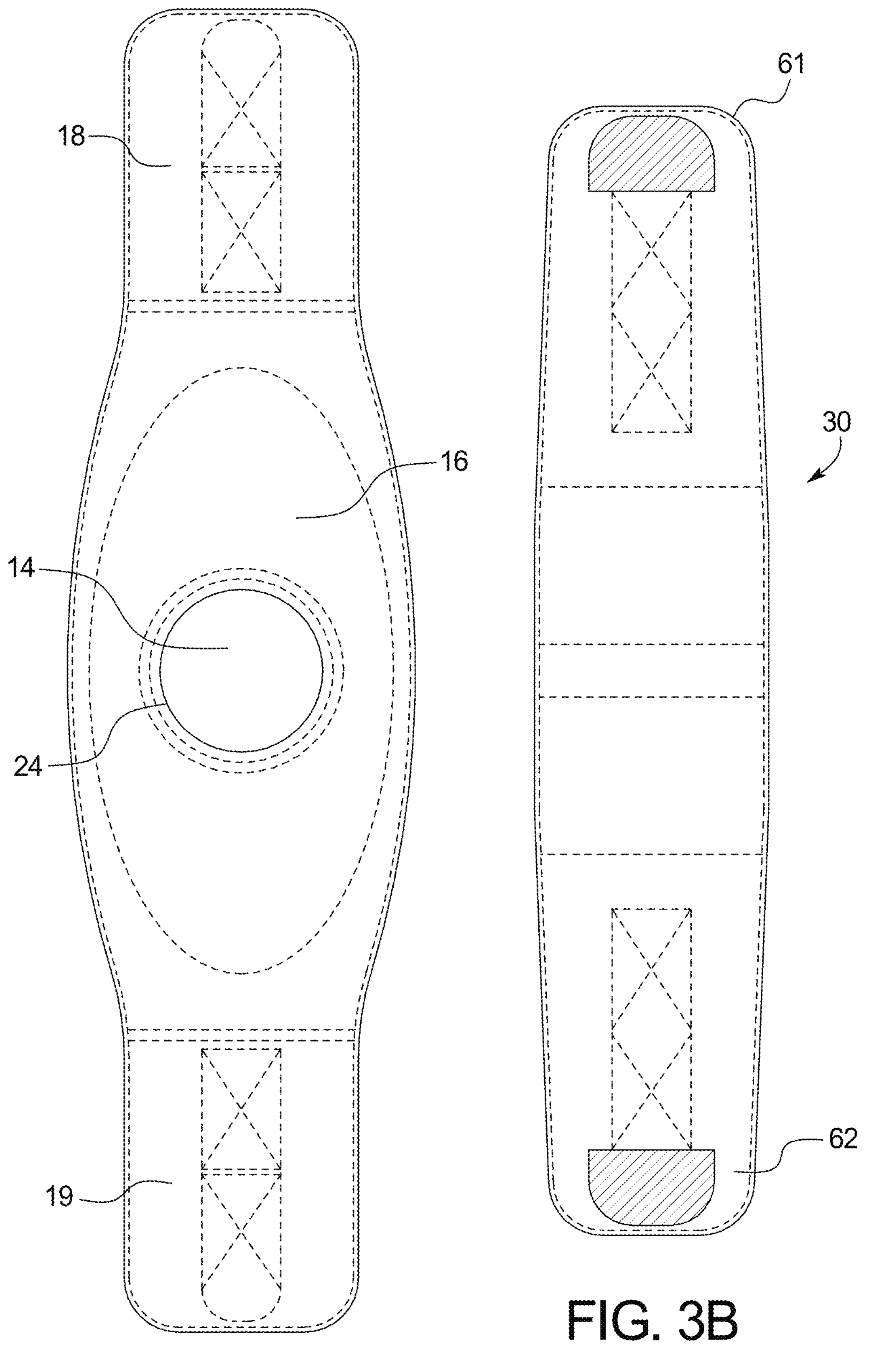
FIGS. 3A-3B is a back view of an example of the hernia belt ostomy support system including a front body portion and back body portion.
Figure 12:
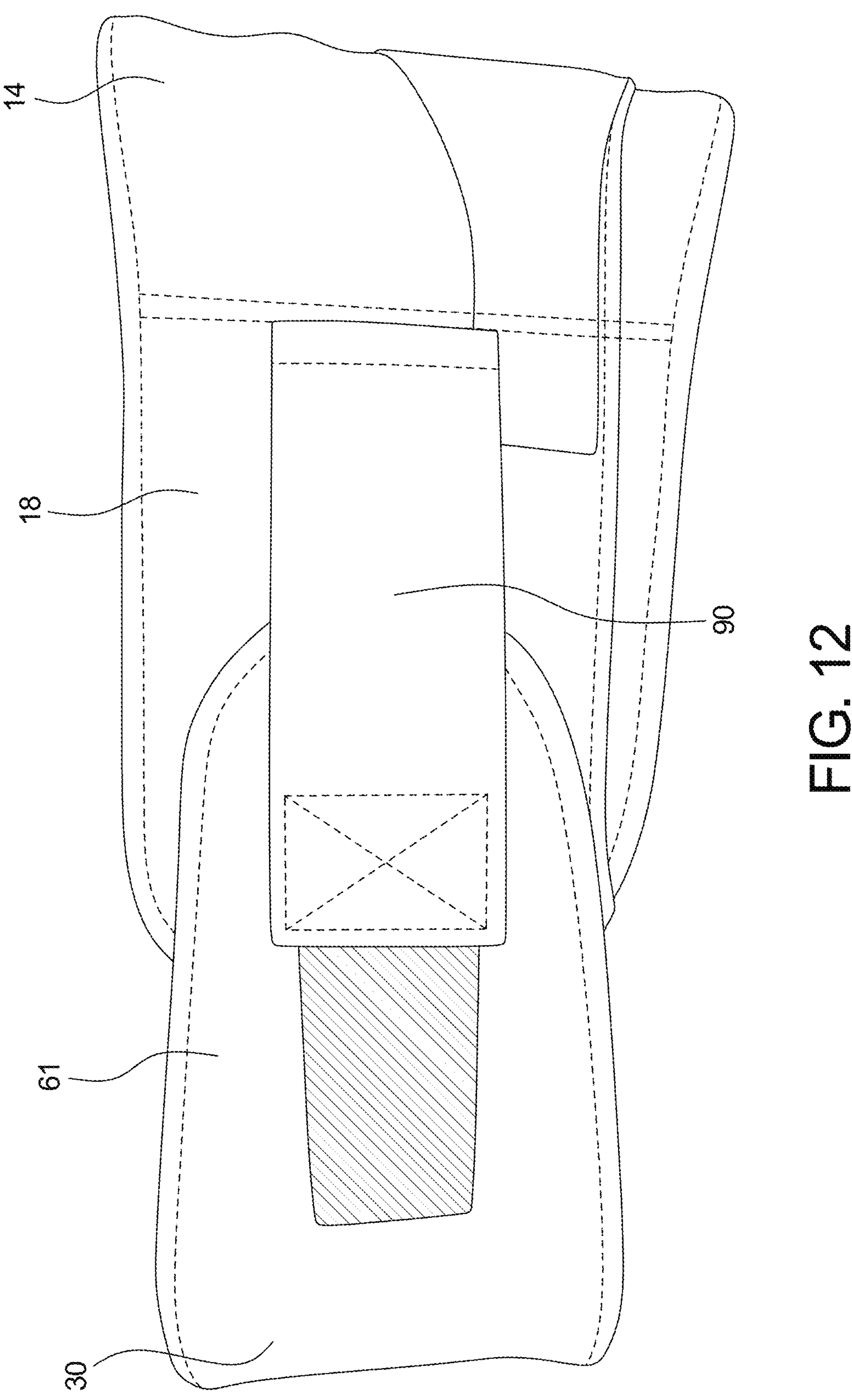
FIG. 12 is a side view of an example of the fastening system disclosed herein.

As shown in FIGS. 3A-3B, the device 10 can be comprised of two separate pieces, such as a front body portion 12 and back body portion 30, wherein a fastener system can be positioned on both ends of the front body portion and both ends of the back body portion such that maximum cinching support capability can be achieved from both the left and right sides evenly. For example, the belt body first end 18 can connect to a back body first end 61, and the belt body second end 19 can connect to a back body second end 62. In an example, the belt body first end 18 and the belt body second end 19 can include a hook and loop fastening system to engage with the back body first end 61 and the back body second end 62, respectively. As shown in FIG. 12, the belt body first end 18 and second end 19 can include a second fastening flap 90 to attach to an external hook and loop system on the outer surface of the belt body first end 18 and second end 19. By adding a double locking closure including the second the hook and loop system, the front body portion 12 cannot be easily separated from the back body portion 30. This creates an added benefit of making sure the device is held securely in place at all times but can still be easily adjusted when desired.

As shown in FIGS. 3A-3B, the back panel 16 of the front body portion 12 can include a stoma opening 24 to provide access to the stoma for the appliance. The back panel 16 can be shaped as an oval with the circular stoma opening 24 in the center. The planar ovular shape of the back panel 16 provides the greatest coverage and support to the hernia. The back panel 16 can include reinforcing material to increase the strength of the back panel 16 while providing elasticity and comfort to the user.

Figure 4:
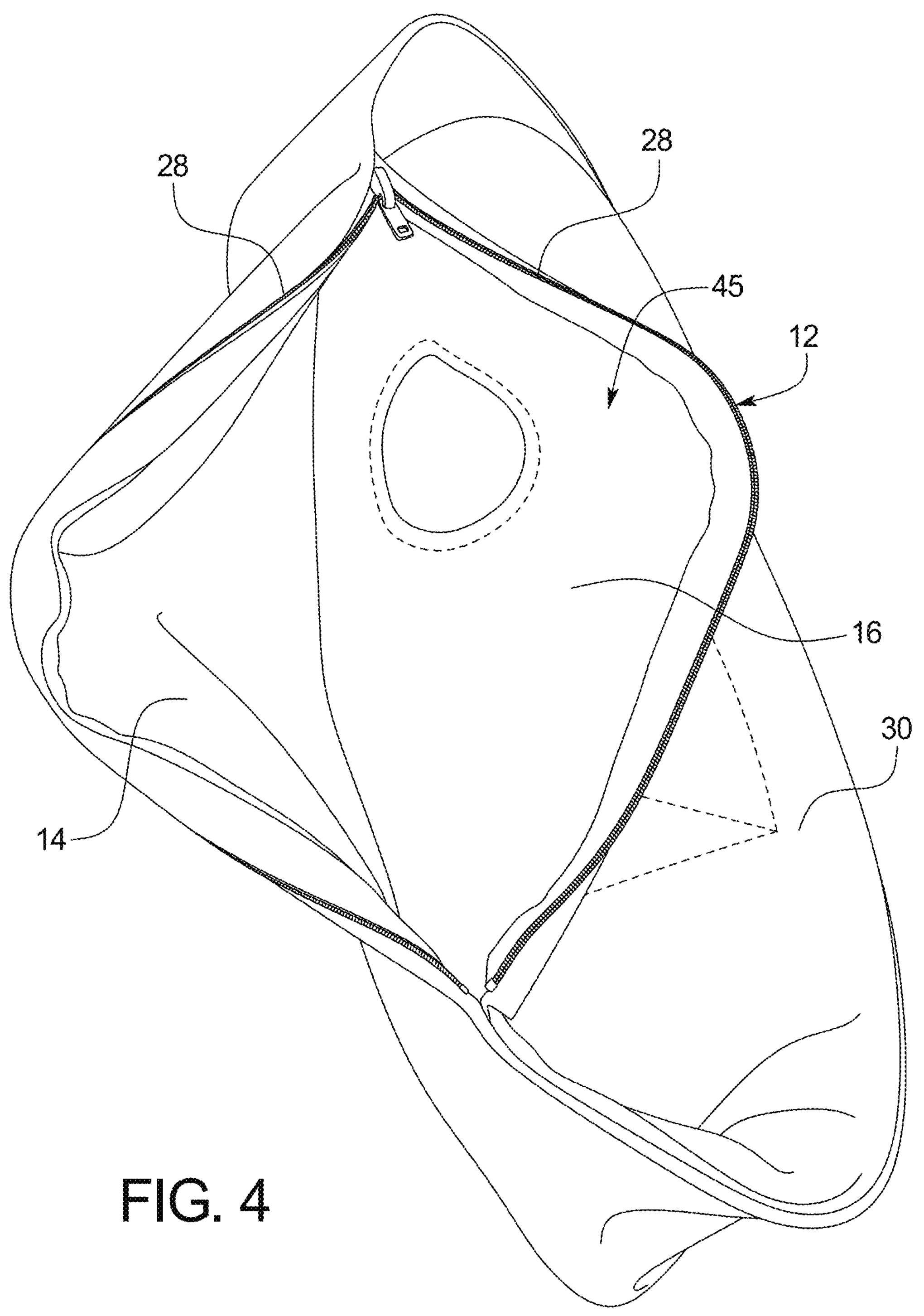
FIG. 4 is a perspective view of an example of the hernia belt ostomy support system illustrating the compartment opening to receive a medical device.
Figure 5:
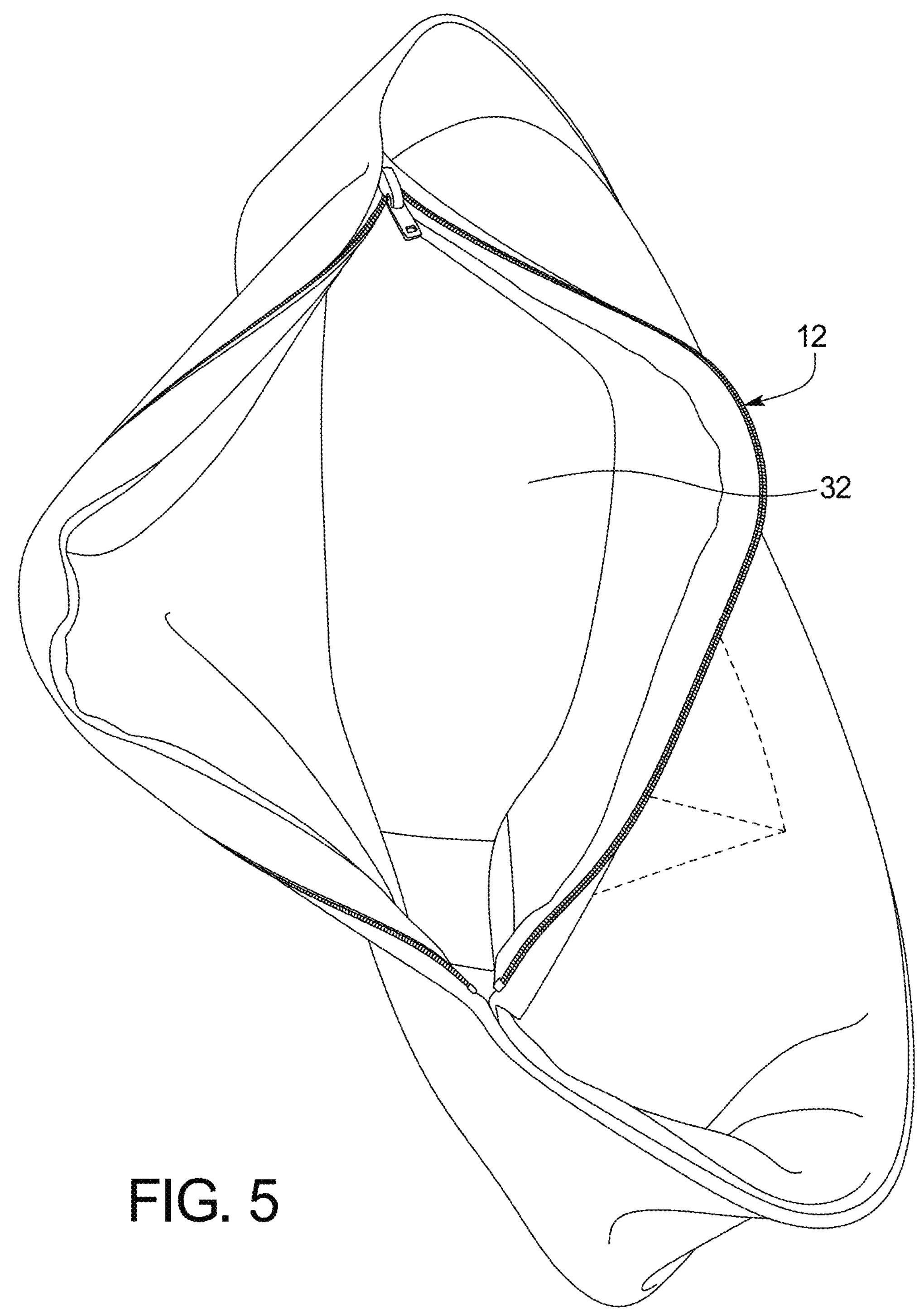
FIG. 5 is a perspective view of an example of the hernia belt ostomy support system illustrating a medical device housed in the compartment opening.

As shown in FIGS. 4-5, the front body portion 12 of the hernia belt ostomy support system 10 includes a compartment system to hold, support and conceal a medical device, such as an ostomy appliance 32, while simultaneously providing hernia support. For example, the belt body (e.g., front body portion 12) can include a front panel 14 and back panel 16 of the front body portion 12, between which additional hernia support stabilizers may be included. In an example, the front panel 14 is outward facing and the back panel 16 is inward facing that fits snug against the body of the wearer.

Figures 6, 7:
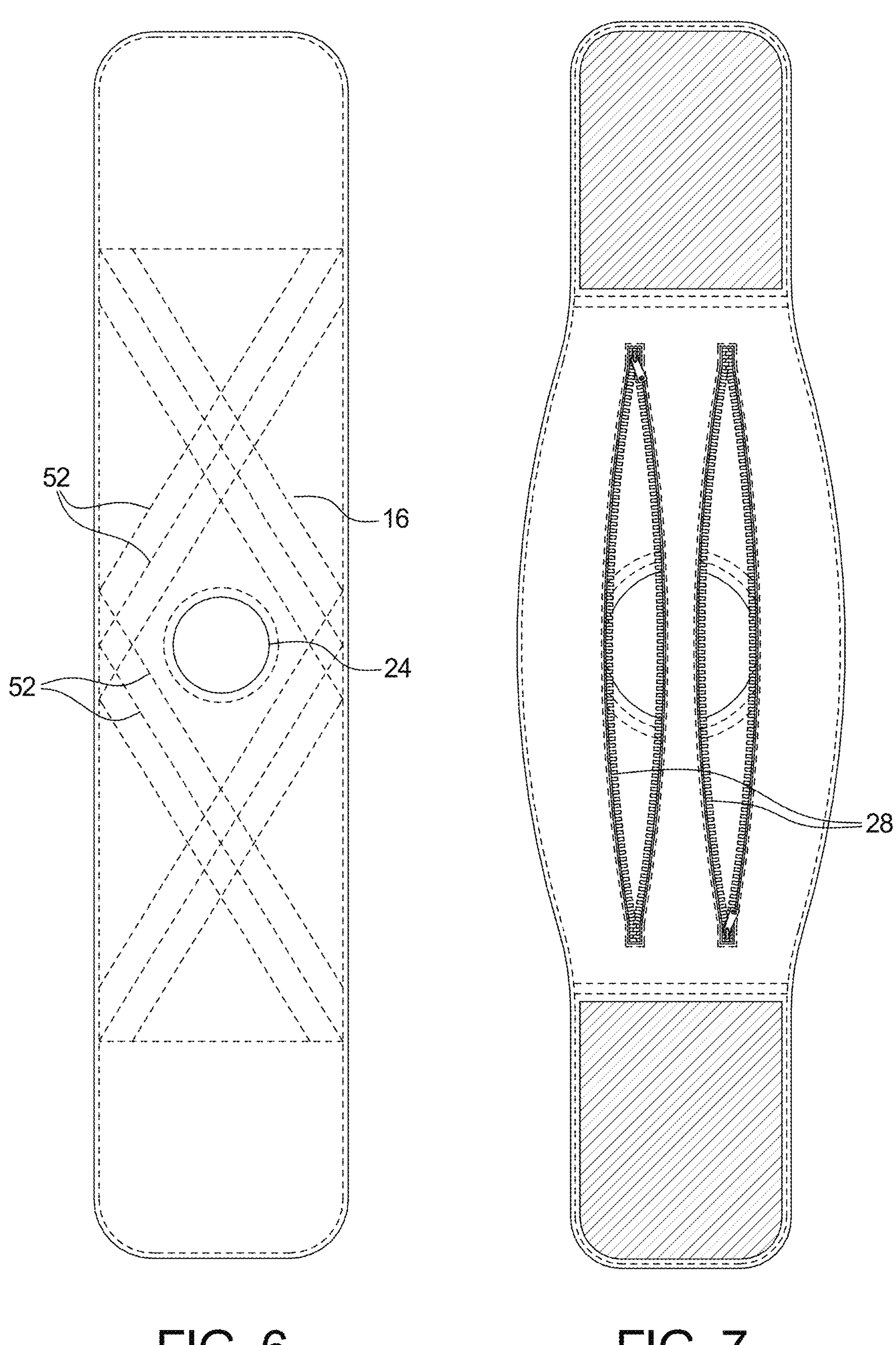
FIG. 6 is a back view of the back panel of the hernia belt ostomy support system including a hernia opening.
FIG. 7 is a front view of an example of the hernia belt ostomy support system illustrating two compartment openings in the front panel.
Figure 10:
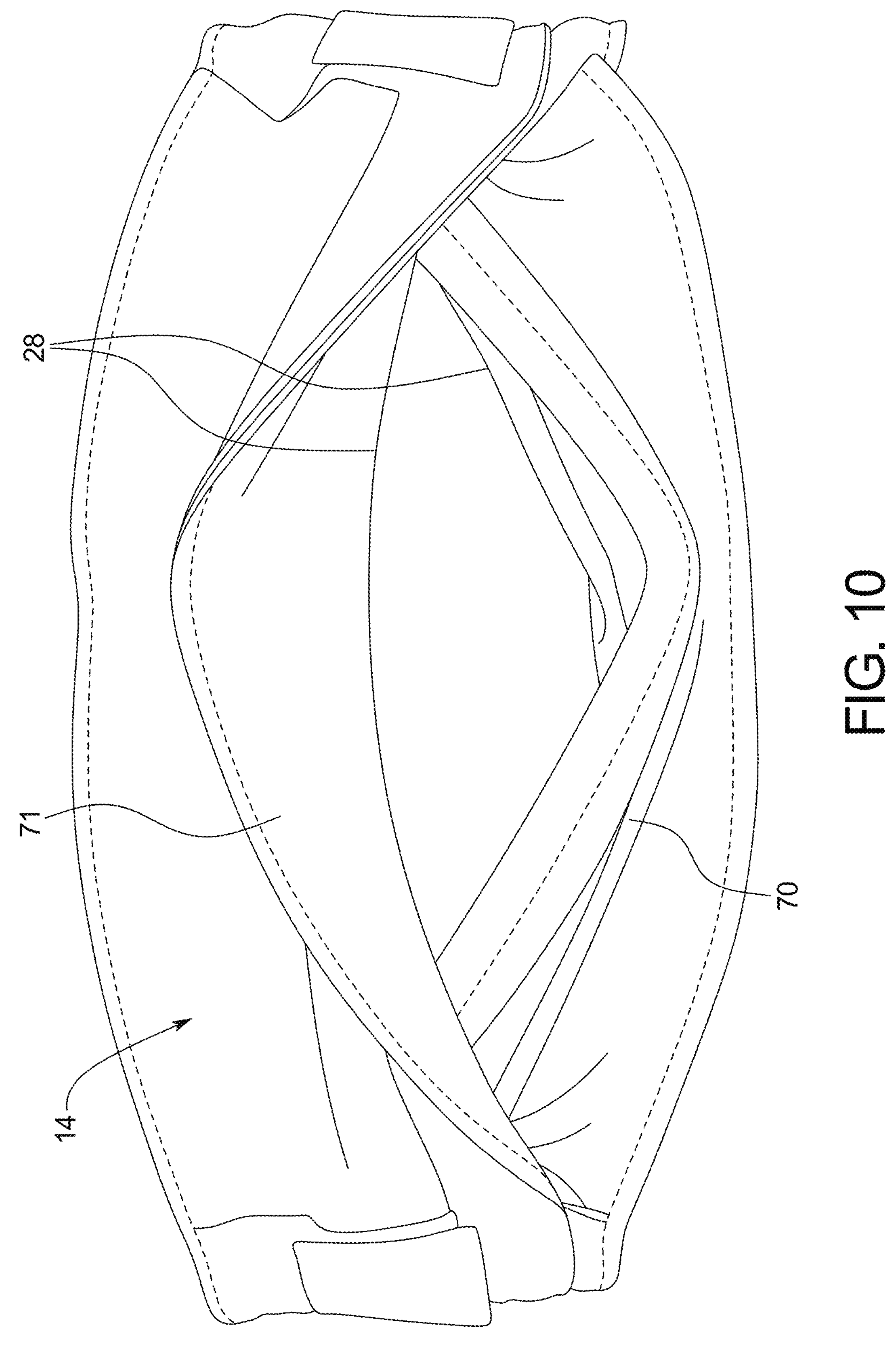
FIG. 10 is a front view of an example of the interior compartment opening.
Figure 11:
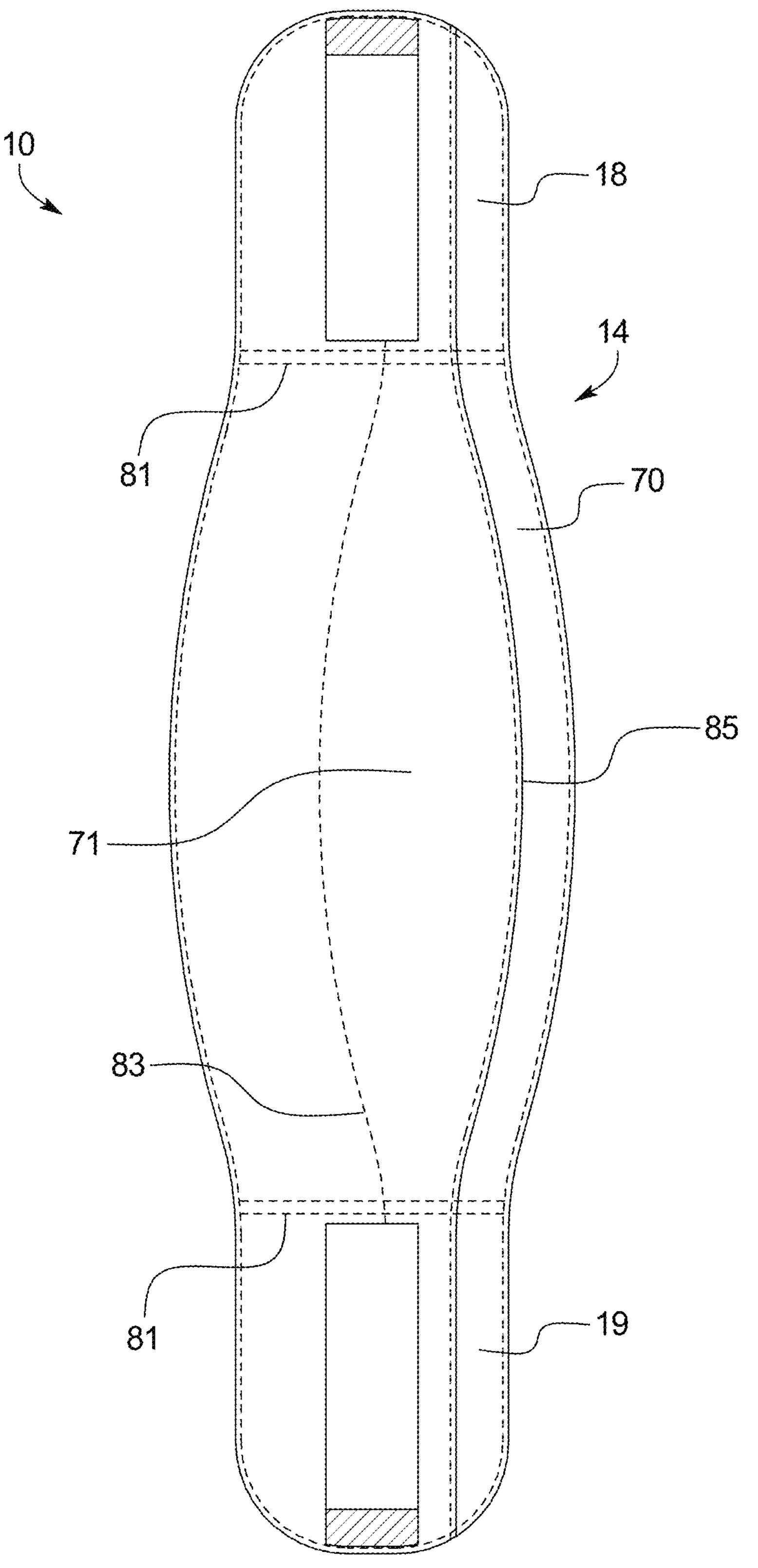
FIG. 11 is a front view of an example of the hernia belt ostomy support system disclosed herein.

The interior compartment cavity 45 can house an ostomy appliance 32, as shown in FIGS. 2 and 5, wherein the compartment cavity 45 is accessible by a compartment opening 28. In an example, as shown in FIGS. 2, 5, and 7, the compartment opening 28 can be positioned on the front panel of the belt body, and in FIG. 4 the compartment opening 28 can be positioned on the upper edge of the compartment cavity 45, wherein the upper edge is where the top edge of the front panel and the top edge of the back panel meet. The compartment opening 28 can include an open seam, elastic seams, zippers, snaps, hook and loop, flaps, among any other suitable fastening or enclosing mechanisms. In an example, the compartment opening 28 can include at least one of a horizontal slit, vertical slit, and/or diagonal slit. As shown in FIGS. 10-11, the compartment cavity 45 can be accessed via pulling apart two flap portions 70, 71 of the front panel 14.

In an example, as shown in FIG. 7, the compartment opening 28 can include two parallel horizontal zippers, wherein a lower zipper allows easy access to the bottom of the pouch area for drainage purposes, wherein an upper zipper allows access from the top of the pouch area downward to enable burping of the bag to release gas. In an example, a vertical pouch system can be used for patients wearing an urostomy option. Further, the pouching system can accommodate more than one compartment, such as a double compartment, for housing multiple types of appliances such as an ostomy, a urostomy, a colostomy, and/or ileostomy appliance.

Figure 9:
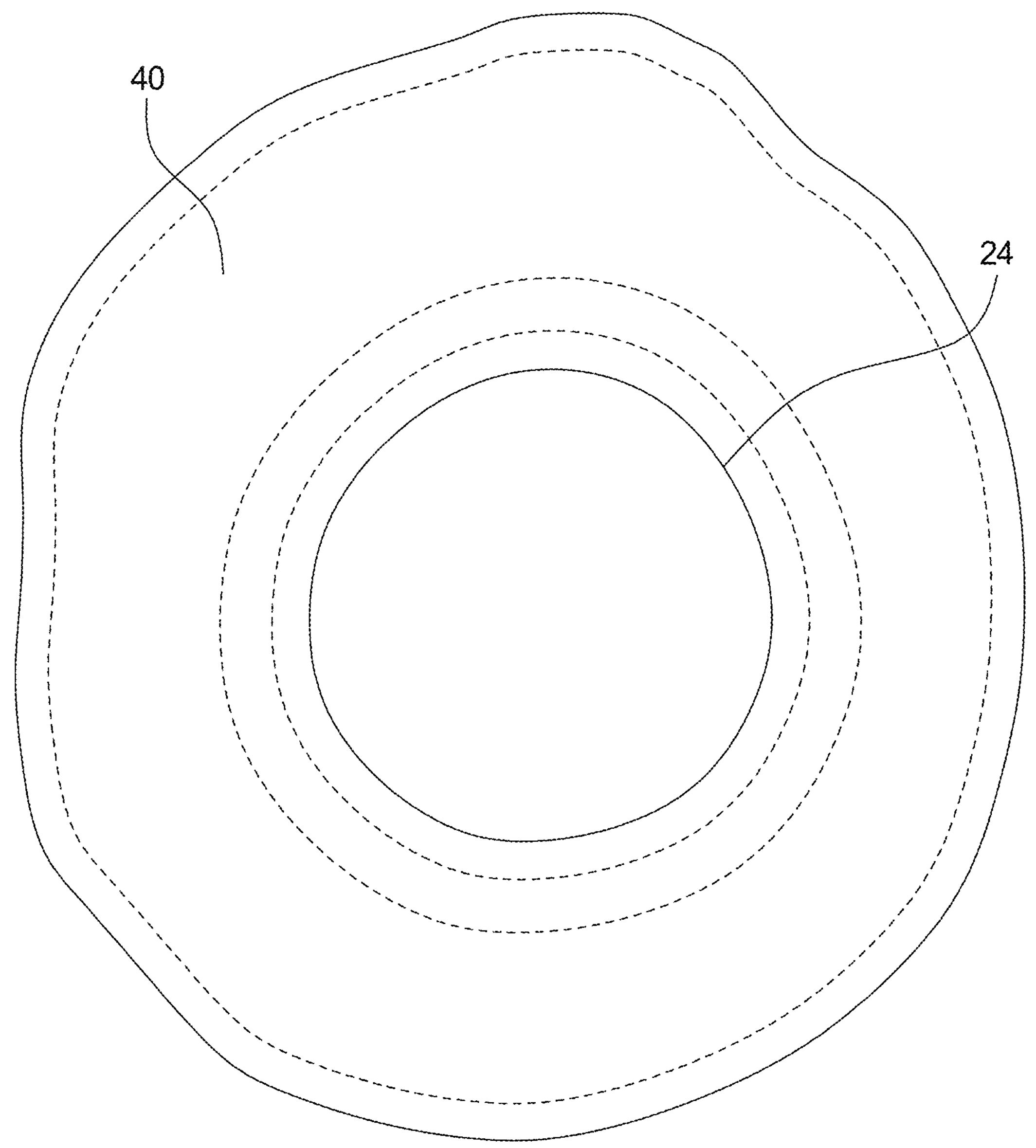
FIG. 9 is a front view of an example of the opening for the stoma illustrating the rim.

As shown in FIGS. 6 and 9, the back panel 16 of the front body portion 12 can include a stoma opening 24 (e.g., a circular cut out within the back panel 16), wherein the stoma opening 24 is provided in different size ring perimeters to easily convert the hole size to a smaller hole. In an example, the stoma opening 24 can include a ring channel 40 inside the perimeter of the stoma opening 24 for receiving a ring (not shown). The solid ring can be positioned inside the fabric along the perimeter of the stoma opening 24. The rings can be provided of different diameters to customize the opening to the user. Alternatively, the ring provided can be adjustable to change the size of the diameter of the ring. In an example, the stoma opening is adjustable.

The stoma opening 24 can be any suitable shape including circular, square, rectangular, a non-symmetrical shape, oblong shape, among others. It is important that there is adequate support around the hole, especially at the top edge of the belt such that the flange patch is not exposed and unsupported. Providing even support around the stoma area is particularly important in order to help prevent the formation of a hernia or to mitigate the effects of an existing hernia.

As shown in FIG. 6, support stitching 52 on the back panel 16 around the stoma opening 24 can provide strength and durability to the support device 10. For example, the support stitching 52 can provide structural integrity to the stoma opening 24. The support stitching 52 can be in any suitable pattern. In an example, the support stitching 52 can include a criss-cross pattern, concentric circles, a grid pattern, among others.

The belt body (e.g., combination of the front body portion 12 and the back body portion 30) can be any suitable size to accommodate a variety of user sizes, and a variety of hernia sizes. For example, the hernia belt 10 can be made in any size, including from 26"-57", and the hernia support panels can have lengths of up to 15", 13", 12", 10", among others. As a result, the device 10 allows for secure cinching to attain the desired tightness for different patients, different hernias, and/or different activities that require more or less support. In an example, the device provides adjustability from both sides of the body.

Figure 8:
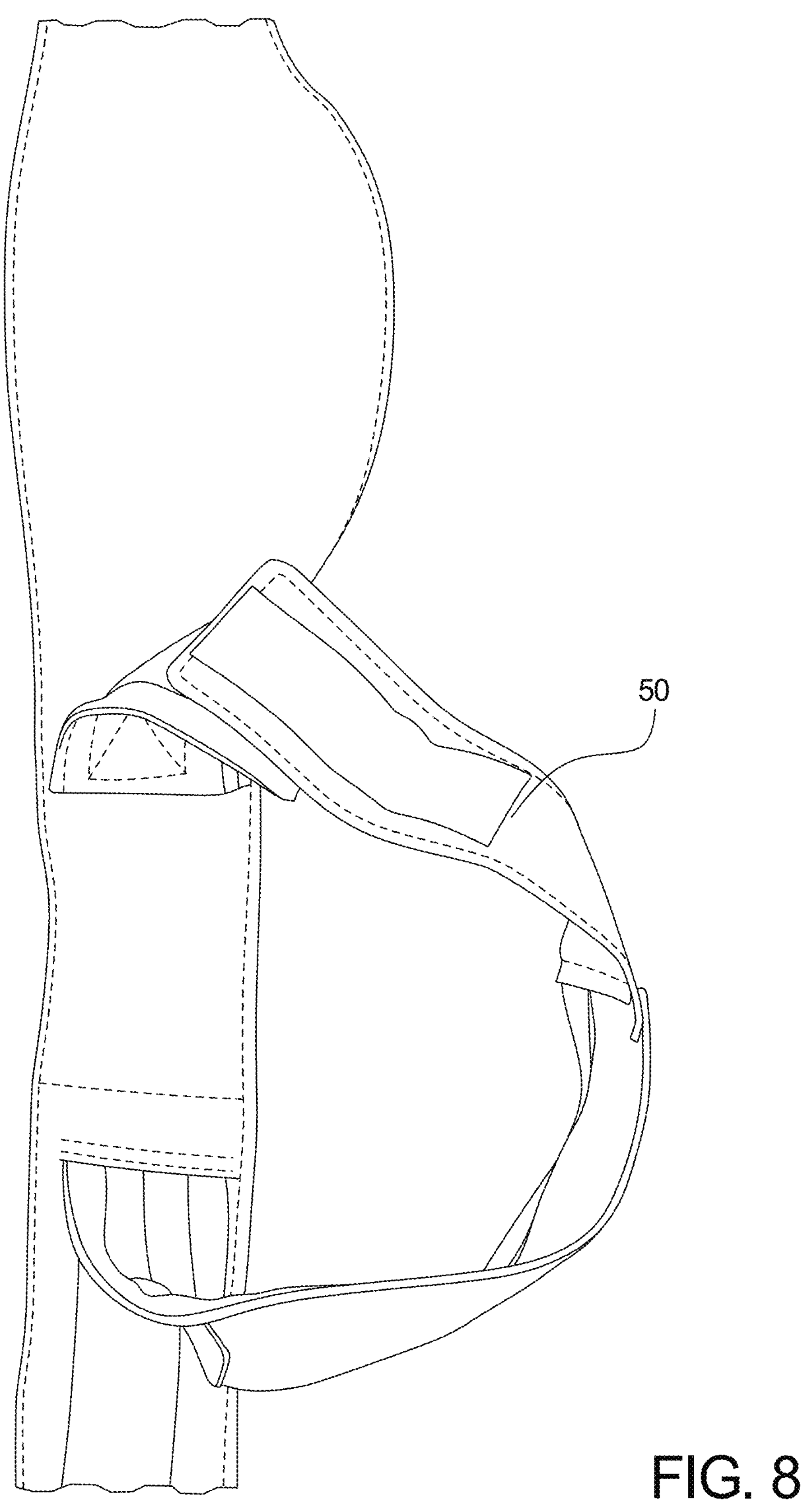
FIG. 8 is a back view of an example of the hernia belt ostomy support system illustrating a support band.

Further, the hernia belt ostomy support system 10 can include any additional securing member. For example, FIG. 8 includes an additional securing band 50 to further secure the hernia support system to the patient's body. As a result, if necessary additional securing strength is needed to support different hernias the belt system can accommodate further adjustments and support. The securing band 50 can be positioned to wrap around the outer surface of the front and back portions of the belt system to apply additional pressure towards the body of the user to further secure the belt system to the body. Alternatively, the securing band 50 can be positioned inside the front and back portions of the hernia belt ostomy support system 10 to secure the hernia belt ostomy support system 10 to the body.

In an example, as shown in FIGS. 10-11, the compartment opening 28 can include a flap opening in the front panel 14 of the front body portion 12. For example, the front panel 14 can include two flap portions 70, 71 that overlap to encase the ostomy appliance. The two flap portions 70, 71 can be pulled away from each other to access the inner compartment. In an example, the first flap portion 71 and/or the second flap portion 70 can include a reinforcement 81 between the front panel 14 and the belt body first end 18 and second end 19 to further increase the support level.

Specifically, the front panel 14 of the front body portion 12 can include a first flap portion 71 to support directly over the stoma as well as adds an additional layer of cushioning to help prevent damage or direct contact with the stoma during daily activities. The protective layer of the first flap portion 71 can add additional protection of the stoma, for example, while leaning over a car as a mechanic, carrying boxes, belt buckles, seat belts etc. The protective layer of the first flap portion 71 can include a curved edge connecting to the front panel 14 such that it directly covers the stoma area and the area directly around the stoma where a hernia would not normally be supported.

The curved seam 83 joining the first flap portion 71 to the front panel 14 in the specific way illustrated in FIG. 11 helps to ensure there is proper stretch so the interior compartment can fill normally and also add support to the pouch area to keep it secure and in place on the patient.

The second flap portion 70 is designed to support an ostomy appliance within the interior compartment. The second flap portion 70 can extend up into a top third of the front panel such that the second flap portion 70 can contain an ostomy appliance within the interior compartment.

An external edge 85 of the first flap portion 71 can be a curved seam and reinforced to provide a cup to fully support the hernia and also to secure an ostomy bag inside the interior compartment. The reinforced strength and design of the external curved seam 85 renders the need of a traditional zipper obsolete. The use of the flap system instead of the zipper is advantageous for some users with arthritis and other physical challenges with dexterity whom may struggle with operating the zipper. The use of the two flap portions makes it very easy to fully access the pouch and hernia area while still wearing the belt. Another benefit of the two flap portions is that there is no metal, making it ideal for travel and metal detectors.

The hernia belt support can be made of any suitable material. In an example, the hernia belt support, or a portion of the hernia belt support, can be made of any natural or synthetic material including but not limited to nylon, Pellon™, Spandex™, Lycra™, among others. In an example, at least a portion of the hernia belt support can include stabilizer 70 weight or other material that can add volume. For example, the front panel 14 and the back panel 16 can include support panels that have a physical volume and tension that provides flexibility, thickness, and strength. Stabilizer fabric can have the characteristic of springing back into place when compressed, then released making the panel self-supporting.

In an example, the materials used for the hernia belt support can be made of water resistant material that can be used in water activities. The material can have wicking properties to prevent the material from becoming heavy in weight due to absorbing water.

In an example, the hernia belt support can be designed to have the appearance of a piece of clothing or accessory (e.g., belt, sash, etc.) that anyone would assume is a normal piece of clothing and not a medical device.

It should be noted that various changes and modifications to the embodiments described herein will be apparent to those skilled in the art. Such changes and modifications may be made without departing from the spirit and scope of the present invention and without diminishing its attendant advantages. For example, various embodiments of the systems and methods may be provided based on various combinations of the features and functions from the subject matter provided herein.

The invention claimed is:

1. A hernia belt ostomy support system comprising:

a belt body including a front body portion and a back body portion, wherein the front body portion includes a front panel, a back panel, and two side portions, wherein the side portions extend from lateral edges of the front panel and the back panel;

a stoma opening within the back panel, wherein the stoma opening is a void within a fabric of the back panel;

an interior compartment between the front panel in the back panel, wherein a front bottom edge of the front panel is connected directly to a back bottom edge of the back panel to form a bottom edge of the interior compartment, and wherein a front top edge of the front panel is connected directly to a back top edge of the back panel to form a top edge of the interior compartment; and a separate securing band to support a hernia and attached to an outer surface of at least one side portion of the belt body, wherein the securing band surrounds an outer surface of the belt body;

wherein at least apportion of one of the bottom edge and the top edge of the interior compartment forms a compartment opening, and wherein the compartment opening includes a zippered closure in which a first side of the zippered closure is attached to the front panel and a second side of the zippered closure is attached to the back panel such that, when zippered, the front panel is connected directly to the back panel by the zippered closure and, when unzipped, the space between the first side of the zippered closure and the second side of the zippered closure form the compartment opening;

when the interior compartment is accessible through the compartment opening along the one of the top edge and the bottom edge of the interior compartment; and wherein the compartment opening defines the only portion of the hernia belt ostomy support system by which either the front bottom edge of the front panel may be separated from the back bottom edge of the back panel or the front top edge of the front panel may be separated from the back top edge of the back panel.

2. The system of claim 1, wherein the side portions include a fastening mechanism to connect ends of the back body portion.

3. The system of claim 2, wherein the fastening mechanism includes a hook and loop fastening system.

4. The system of claim 1, wherein an outer surface of the side portions includes a fastening flap, wherein the fastening flap includes a hook and loop fastening system on an inner surface thereof, and wherein the hook and loop fastening system is configured to attach to a hook and loop fastening system on an outer surface of the side portions.

5. The system of claim 1, wherein the interior compartment houses an ostomy appliance.

6. The system of claim 1, wherein the stoma opening includes a ring channel along the perimeter of the stoma opening.

7. The system of claim 6, further comprising a ring inside the ring channel of the stoma opening.

8. The system of claim 1, wherein the back panel includes a support stabilizer.

9. The system of claim 1, wherein the back panel includes support stitching in a crisscross pattern surrounding the stoma opening.

10. The system of claim 1, wherein the back panel includes support stitching of concentric circles surrounding the stoma opening.

11. The system of claim 1 wherein a length of the securing band is adjustable.

12. The system of claim 1, wherein the separate securing band wraps around an outer surface of the belt body.

* * * * *